United States Patent
Chin et al.

(10) Patent No.: US 8,506,474 B2
(45) Date of Patent: Aug. 13, 2013

(54) METHOD AND DEVICE FOR TREATING DYSFUNCTIONAL CARDIAC TISSUE

(75) Inventors: Sing-Fatt Chin, Union City, CA (US); Lon Annest, New York, NY (US); Robert O'Reilly, Lafayette, CA (US)

(73) Assignee: BioVentrix, Inc., San Ramon, CA (US)

( * ) Notice: Subject to any disclaimer, the term of this patent is extended or adjusted under 35 U.S.C. 154(b) by 1072 days.

(21) Appl. No.: 11/507,146

(22) Filed: Aug. 21, 2006

(65) Prior Publication Data

US 2007/0073274 A1 Mar. 29, 2007

Related U.S. Application Data

(60) Provisional application No. 60/709,730, filed on Aug. 19, 2005, provisional application No. 60/709,690, filed on Aug. 19, 2005, provisional application No. 60/711,727, filed on Aug. 26, 2005.

(51) Int. Cl.
*A61F 2/00* (2006.01)

(52) U.S. Cl.
USPC .............................................. 600/37; 600/16

(58) Field of Classification Search
USPC .................. 600/16–18, 37; 128/897–898
See application file for complete search history.

(56) References Cited

U.S. PATENT DOCUMENTS

| | | | |
|---|---|---|---|
| 4,007,743 A | 2/1977 | Blake | |
| 5,295,958 A | 3/1994 | Shturman | |
| 5,830,224 A | 11/1998 | Cohn et al. | |
| 5,961,440 A | 10/1999 | Schweich, Jr. et al. | |
| 6,045,497 A | * 4/2000 | Schweich et al. | 600/16 |
| 6,050,936 A | 4/2000 | Schweich, Jr. et al. | |
| 6,059,715 A | 5/2000 | Schweich, Jr. et al. | |
| 6,125,852 A | 10/2000 | Stevens et al. | |
| 6,162,168 A | 12/2000 | Schweich, Jr. et al. | |

(Continued)

FOREIGN PATENT DOCUMENTS

| | | |
|---|---|---|
| EP | 1 078 644 A1 | 2/2001 |
| WO | 00/06028 A1 | 2/2000 |
| WO | 02/30335 A2 | 4/2002 |
| WO | 2007/022519 A2 | 2/2007 |

OTHER PUBLICATIONS

International Search Report and Written Opinion of PCT Application No. PCT/US06/22594, dated Oct. 1, 2008, 9 pages total.

(Continued)

*Primary Examiner* — Charles A Marmor, II
*Assistant Examiner* — Carrie R Dorna
(74) *Attorney, Agent, or Firm* — Kilpatrick Townsend & Stockton LLP

(57) ABSTRACT

Various methods and devices are provided for reducing the volume of the ventricles of the heart. In one embodiment, a method for reducing the ventricular volume of a heart chamber is provided including the steps of inserting an anchoring mechanism onto dysfunctional cardiac tissue, deploying one or more anchors into the dysfunctional cardiac tissue, raising the dysfunctional cardiac tissue using the anchors, and securing the anchors to hold the dysfunctional cardiac tissue in place. Further, a device for reducing the volume of the ventricles of a heart chamber is provided where the device has one or more clips for placement on dysfunctional cardiac tissue of a heart, one or more anchors for deployment and securement into the dysfunctional cardiac tissue, and a lifting mechanism for raising the one or more anchors and the dysfunctional cardiac tissue.

8 Claims, 9 Drawing Sheets

(56) References Cited

U.S. PATENT DOCUMENTS

| | | | |
|---|---|---|---|
| 6,165,119 | A | 12/2000 | Schweich, Jr. et al. |
| 6,166,684 | A | 12/2000 | Yoshikawa et al. |
| 6,258,021 | B1 | 7/2001 | Wilk |
| 6,260,552 | B1 | 7/2001 | Mortier et al. |
| 6,406,420 | B1 | 6/2002 | McCarthy et al. |
| 6,494,825 | B1 | 12/2002 | Talpade |
| 6,572,529 | B2 | 6/2003 | Wilk |
| 6,616,684 | B1 | 9/2003 | Vidlund et al. |
| 6,709,382 | B1 | 3/2004 | Horner |
| 6,746,471 | B2 | 6/2004 | Mortier et al. |
| 6,776,754 | B1 | 8/2004 | Wilk |
| 6,808,488 | B2 | 10/2004 | Mortier |
| 7,146,225 | B2 | 12/2006 | Guenst et al. |
| 7,753,923 | B2 | 7/2010 | St. Goar et al. |
| 7,766,816 | B2 * | 8/2010 | Chin et al. ............ 600/37 |
| 7,785,248 | B2 | 8/2010 | Annest et al. |
| 8,123,668 | B2 | 2/2012 | Annest et al. |
| 2001/0041821 | A1 * | 11/2001 | Wilk ....................... 600/16 |
| 2002/0058855 | A1 | 5/2002 | Schweich, Jr. et al. |
| 2002/0077524 | A1 | 6/2002 | Schweich, Jr. et al. |
| 2002/0120298 | A1 | 8/2002 | Kramer et al. |
| 2002/0123768 | A1 | 9/2002 | Gilkerson et al. |
| 2002/0169359 | A1 | 11/2002 | McCarthy et al. |
| 2002/0169360 | A1 * | 11/2002 | Taylor et al. ............ 600/37 |
| 2002/0188170 | A1 | 12/2002 | Santamore et al. |
| 2003/0032979 | A1 | 2/2003 | Mortier et al. |
| 2003/0163165 | A1 | 8/2003 | Bornzin et al. |
| 2003/0166992 | A1 | 9/2003 | Schweich, Jr. et al. |
| 2003/0181951 | A1 | 9/2003 | Cates |
| 2004/0167580 | A1 | 8/2004 | Mann et al. |
| 2004/0225304 | A1 | 11/2004 | Vidlund et al. |
| 2005/0065506 | A1 | 3/2005 | Phan |
| 2005/0096498 | A1 | 5/2005 | Houser et al. |
| 2005/0288613 | A1 | 12/2005 | Heil, Jr. |
| 2006/0135962 | A1 | 6/2006 | Kick et al. |
| 2006/0161040 | A1 | 7/2006 | McCarthy et al. |
| 2006/0161238 | A1 | 7/2006 | Hall |
| 2006/0241340 | A1 | 10/2006 | Schroeder et al. |
| 2006/0247672 | A1 | 11/2006 | Vidlund et al. |
| 2007/0010876 | A1 | 1/2007 | Salahieh et al. |
| 2007/0049971 | A1 | 3/2007 | Chin et al. |
| 2007/0055303 | A1 | 3/2007 | Vidlund et al. |
| 2007/0112244 | A1 | 5/2007 | McCarthy et al. |
| 2007/0203503 | A1 | 8/2007 | Salahieh et al. |
| 2008/0097148 | A1 | 4/2008 | Chin et al. |
| 2008/0294251 | A1 | 11/2008 | Annest et al. |
| 2009/0093670 | A1 | 4/2009 | Annest et al. |
| 2010/0416655 | | 1/2010 | Arnest et al. |
| 2010/0268020 | A1 | 10/2010 | Chin et al. |
| 2011/0160750 | A1 | 6/2011 | Annest et al. |
| 2012/0190958 | A1 | 7/2012 | Annest et al. |

OTHER PUBLICATIONS

U.S. Appl. No. 11/450,131—Requirement for Restriction / Elections mailed Oct. 16, 2008, 6 pages total.

U.S. Appl. No. 11/450,131—Response to Restriction Requirement mailed Nov. 17, 2008, 8 pages total.

U.S. Appl. No. 11/450,131—Requirement for Restriction / Elections mailed Feb. 23, 2009, 6 pages total.

U.S. Appl. No. 11/450,131—Response to Restriction Requirement mailed May 21, 2009, 4 pages total.

U.S. Appl. No. 11/450,131—Office Action mailed Aug. 6, 2009, 15 pages total.

European Examination Report of EP Patent Application 05810316.9 dated Mar. 10, 2009, 6 pages.

International Search Report and Written Opinion of PCT Application No. PCT/US2005/036690, mailed Jul. 9, 2007, 6 pages.

International Search Report and Written Opinion of PCT Application No. PCT/US09/51288, mailed Sep. 15, 2009, 9 pages.

International Search Report and Written Opinion of PCT Application No. PCT/US08/64255, mailed Sep. 29, 2008, 17 pages.

International Search Report and Written Opinion of PCT Application No. PCT/US06/22594, mailed Oct. 1, 2008, 9 pages.

International Search Report and Written Opinion of PCT Application No. PCT/US08/78810, mailed Feb. 12, 2009, 11 pages.

* cited by examiner

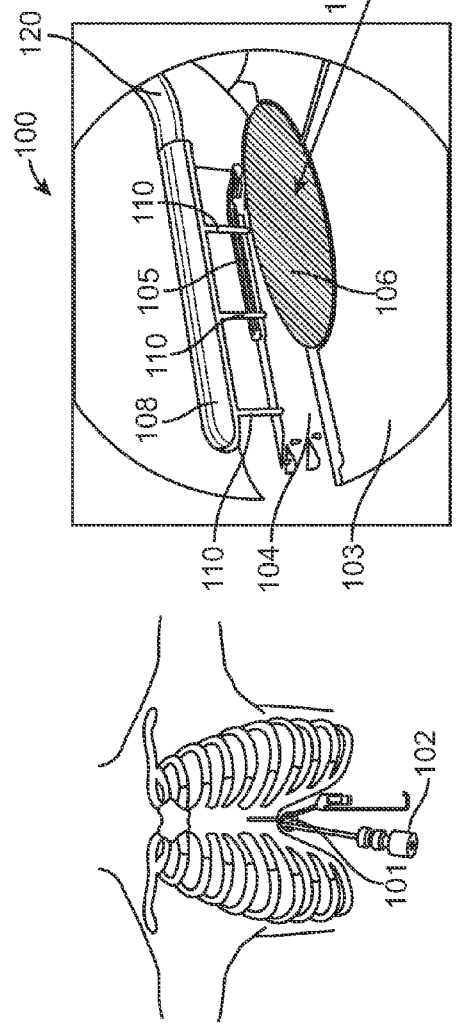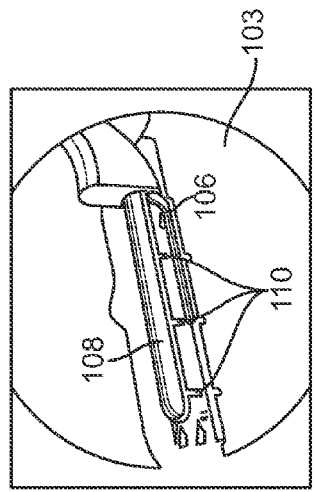

PATCH W/ DEFORMABLE SLIT

METHOD AND DEVICE FOR TREATING DYSFUNCTIONAL CARDIAC TISSUE

This application claims the benefit of provisional patent application Ser. Nos. 60/709,730 filed on Aug. 19, 2005, Ser. No. 60/709,690 filed on Aug. 19, 2005 and Ser. No. 60/711,727 filed on Aug. 26, 2005.

BACKGROUND OF THE INVENTION

1. Field of the Invention

This invention relates generally to devices for resizing ventricle and related methods for placing the devices. More particularly, it relates to sizing devices for reducing the ventricular volume to improve the heart's pumping action. The devices and methods of the present invention are directed toward thoracoscopy or subxiphoid techniques used to facilitate sizing of the ventricles.

2. Prior Art

Heart failure (HF), the heart's inability to pump an adequate volume of blood to the tissues, is the only major cardiovascular condition that continues to increase in incidence in the United States. Approximately 5 million patients are currently diagnosed with HF in the United States. The American Heart Association estimates that 550,000 new HF cases develop each year. This condition is responsible for an estimated 900,000 hospitalizations annually—more than any other medical condition among the elderly. Approximately 6.5 million hospital days each year are attributed to and related to HF, and as many as one third of those patients are readmitted for treatment of symptom recurrence within 90 days. Thus, it is not surprising that the cost of providing advanced medical care for the millions of patients suffering from HF is extraordinarily high—now estimated at more than $38 billion annually.

In certain pathological conditions, the ventricles of the heart become ineffective in pumping the blood, causing a back-up of pressure in the vascular system behind the ventricle. The reduced effectiveness of the heart is usually due to an enlargement of the heart. Coronary artery disease causes approximately 60% of congestive heart failure. Acute myocardial infarction (AMI) due to obstruction of a coronary artery is a common initiating event that can lead ultimately to heart failure. A myocardial ischemia may, for example, cause a portion of a myocardium of the heart to lose its ability to contract. Prolonged ischemia can lead to infarction of a portion of the myocardium (heart muscle) wherein the heart muscle dies and becomes scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the hearts ability to move blood forward. When local wall motion moves in this way it is said to be dyskinetic. The dyskinetic portion of the myocardium may stretch and eventually form an aneurysmic bulge.

One problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. In response, the heart tissue remodels to accommodate the chronically increased filling pressures, further increasing the work that the now-compromised myocardium must perform. This vicious cycle of cardiac failure results in the symptoms of congestive heart failure such as shortness of breath on exertion, edema in the periphery, nocturnal dypsnia (a characteristic shortness of breath that occurs at night after going to bed), weight gain, and fatigue, to name a few. The increase in wall stress also occurs during diastolic filling. The stress increase requires a larger among of oxygen supply, which can result in exhaustion of the myocardium leading to a reduced cardiac output of the heart.

The incidence of ischemic dilated cardiomyopathy is increasing, not only as a consequence of the aging of the population, but also because effective emergency interventions for otherwise fatal acute coronary events are extending the lives of many patients with ischemic congestive heart failure (CHF). Despite the major advances in both medical and surgical therapy, the management of patients with coronary artery disease and left ventricular (LV) dysfunction continues to be challenging due to the complex and multifactorial pathophysiology of this condition.

Since heart transplantation, when indicated, continues to be limited by several factors, conventional surgical treatment for ischemic cardiomyopathy has gained increasing attention in recent years and a variety of therapeutic interventions have been developed or optimized.

It has been demonstrated that myocardial revascularization and valve repair are capable of improving left ventricular function.

Recent efforts have concentrated on improving left ventricular function by means of surgical methods aimed at ventriculoplasty with or without a reduction in ventricular volume.

Prior treatments for heart failure associated with such dilatation fall into three general categories. The first being pharmacological treatment, for example, diuretics and ACE inhibitors. The second being assist devices, for example, pumps. Finally, effective surgical treatments also have been performed with, for example, the Dor or Jatene procedure, or left ventricular reconstruction (LVR), which requires the use of cardiopulmonary bypass (CPB) machine.

Many patients who would benefit from left ventricular reconstruction are the least likely to withstand the effects of CPB due to age, poor ejection fraction, or other cardiovascular disease. Therefore, there remains a need for an efficient device and method for reducing ventricular volume.

SUMMARY OF THE INVENTION

This invention relates to a device and method for completely off-pump treatment of congestive heart failure patients, and particularly, a sizing device and method for excluding infarcted tissue and reducing ventricular volume. The device and method may be performed minimally invasively which is less traumatic to the patient than an open-chest and open-heart surgical technique.

Thus, a more recent technique for treating the various forms of heart failure discussed above includes placing devices on the heart to exclude infarcted tissue and to reduce the ventricular volume. The devices are configured to reduce the ventricular volume, hence to reduce the tension in the heart wall, and thereby reverse the disease process of a failing heart.

An aspect of the present invention pertains to a clip or clamp device, and related clip methods, for thoracoscopic device placement on the heart. The clips of the present invention may be placed thoracoscopically. The inventive techniques and devices thus are minimally invasive and less risky to patients.

According to an aspect of the invention, a method for placing the clip assembly anterior a heart chamber around the infarcted tissue comprises providing a flexible and strong member having a clip or clamp and a deployable anchoring assembly connected to at least one end. The method further includes advancing an anchoring member through vasculature structure and into the heart chamber such that the first end of the anchoring member extends through infracted tissue of a wall through the heart chamber wall and pulling the infarcted tissue into or around the clip or clamp to exclude the dysfunctional tissue to reduce ventricular volume.

Yet another aspect of the invention includes a delivery tool for delivering a transventricular volume reduction device to chamber of the heart, comprising a tubular member having a distal end and proximal end, the distal end having an anchoring element and the tube defining a lumen or suture configured to carry at least a portion of the anchoring assembly. The delivery tool further includes at least one support mechanism disposed proximate the distal end of the tubular member, the support mechanism being configured to stabilize the tubular member with respect to a heart wall surrounding the chamber. The tubular member is configured to be advanced through vasculature structure and into the heart chamber.

In view of the above need for treating the dysfunctional tissue, the present invention provides a system and method incorporated into the clip or clamp device and employs small quantities of a drug to be administered over an extended period of time to the heart tissues. The methods of the present invention thus avoid the pitfalls associated with systemic delivery of a drug.

A further advantage of the present invention is that it avoids problems associated with bolus injection of a drug, such as delivery of an amount of drug to the cardiac tissue, which is too high and which therefore may have deleterious effects on the cardiac tissue.

Another advantage is that it provides long-term delivery of a drug to the pericardium or myocardial tissue, with even delivery rate.

Still another important advantage is that extended delivery of a drug to the cardiac tissue can be achieved during the placement of clip or clamp for dysfunctional tissue exclusion, without the need for invasive surgery, thereby reducing trauma to the patient.

Further, in view of the above need of treating the dysfunctional tissue, the present invention provides a system and method incorporated into the clip or clamp employing transducers/sensors for determining the heart function and parameter and measuring heart performance of both left and right ventricles, particularly the left ventricle without requiring invasive surgery to access the left ventricle.

The sensors comprise at least a first sonomicrometer piezoelectric crystal mounted on a clip or clamp, so that when the clip or clamp is implanted on the heart chamber, so does the sensor. One or more additional sonomicrometer piezoelectric crystals can be mounted on the clip or clamp, such that the distance between the three or more sonomicrometer crystals can be determined. In each case, the sonomicrometer crystals are distributed about a heart chamber of interest such that the distance between the separated ultrasound transmitter and receiver crystal pairs changes with contraction and relaxation of the heart chamber.

The invention thus involves the incorporation of sonomicrometer piezoelectric crystals into the clip or clamp.

A principal advantage of the system and method of the present invention includes the ability to directly monitor left ventricular function without opening the left side of the heart. The system and method of the present invention is advantageously employed to measure cardiac dimensions in real time and to either record or transmit these values for monitoring purposes or to use these values as feedback to modify the delivery of electrical or pharmacological therapy, particularly in the treatment of heart failure.

The system and method of the present invention can be advantageously employed in the detection of electromechanical association during pacing or arrhythmias, differentiation of hemodynamically significant and insignificant ventricular tachycardias, monitoring of cardiac output, ventricular volume, determining the need for aggressive and less aggressive pharmacological therapies, and the like.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIGS. 1-9 illustrate an anchoring system used for reducing ventricular volume of a heart in accordance with an embodiment of the present invention;

DETAILED DESCRIPTION OF THE INVENTION

Figure 4:
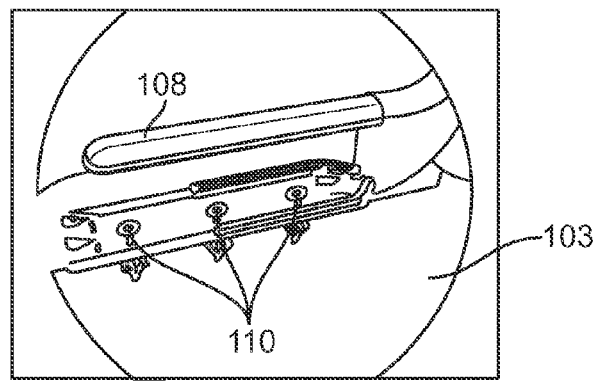

Although this invention is applicable to numerous and various types of cardiovascular methods, it has been found particularly useful in the field of reducing ventricular volume of the heart. Therefore, without limiting the applicability of the invention to the above, the invention will be described in such environment.

With reference to FIGS. 1-9, an anchoring system in accordance with one embodiment of the present invention will be described.

Initially, in FIG. 1, a subxiphoid incision is cut to create an opening 101 to access the ventricles of the heart. Additional access may be performed in the intercostal space for other instruments as well. Then, a double balloon catheter 102 is introduced into the heart through the opening 101 to unload the heart. The balloon catheter 102 provides inflow occlusion to decompress the ventricles, thereby reducing the systolic pressure for aid in reducing the ventricular volume or exclusion of dysfunctional cardiac tissue. The catheter 102 can be placed surgically in an open chest or via femoral or subclavian veins percutaneously.

As seen in FIG. 2, an anchoring mechanism 100 is then inserted through a delivery tool 120. The delivery tool 120 comprises a tubular member having a distal end and proximal end, the distal end having the anchoring mechanism 100 protruding from it. The tubular member is configured to be advanced through vasculature structure and into the heart chamber.

The anchoring mechanism 100 is brought through the delivery tool 120 and then positioned on an epicardial surface where the dysfunctional cardiac tissue 103 is located. The anchoring mechanism 100 can have a flexible bottom portion 104 with clips 105, 106, and a top portion 108 with one or more anchors 110. The clip 106 has a bottom surface 106a having pods 107, which can be seen clearly in FIG. 2b, which shows a cross sectional view of the clips 105, 106 with pods 107. The pods can be used to deliver hear failure drugs such as bet blocker, ACE, ARB, etc., which can be released slowly onto the dysfunctional cardiac tissue 103.

Further, several sonomicrometer crystals sensors (not shown) are located on the clips 105, 106 which are implanted in or on the patient's heart. The sensors are used for determining the heart function and parameter and measuring heart performance of both the left and right ventricles. The sensors comprise at least a first sonomicrometer piezoelectric crystal mounted on the clips 105, so that when the one or more clips 105 are implanted on the heart chamber, so are the sensors. One or more additional sonomicrometer piezoelectric crystals can be mounted on the clips 105, such that the distance between the sonomicrometer crystals can be determined. In each case, the sonomicrometer crystal are distributed about a heart chamber of interest such that the distance between the separated ultrasound transmitter and receiver crystal pairs changes with contraction and relaxation of the heart chamber.

Figure 5:
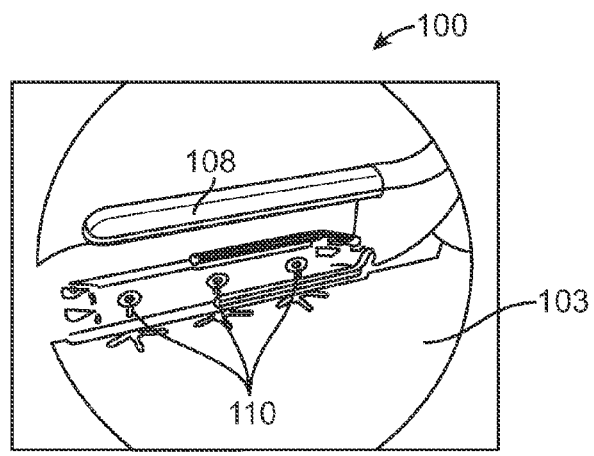

Then, as shown in FIG. 3, the anchoring mechanism 100 is inserted in the dysfunctional tissue 103. The top portion 108 is used to insert the anchors 110 through the dysfunctional tissue 103 and into the heart chamber such that a bottom end of the anchors 110 extends through the infarcted tissue into or around the clips 105. As seen in FIG. 4, the anchors 110 are slowly deployed into the dysfunctional tissue 103. In FIG. 5, anchor deployment is completed and the anchors 110 are locked into the dysfunctional tissue 103. The anchors 110 have a bottom end that deploys such that once it goes through the dysfunctional cardiac tissue 103 it opens up to secure itself to the dysfunctional cardiac tissue 103.

Figure 6:
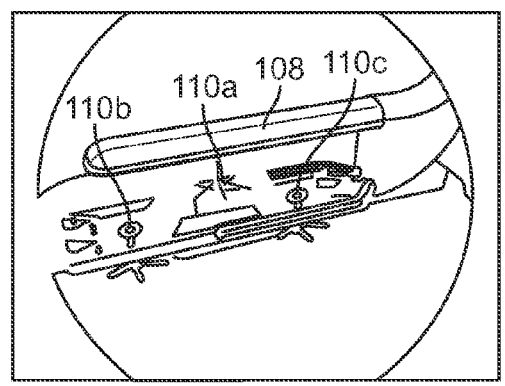
Figure 7:
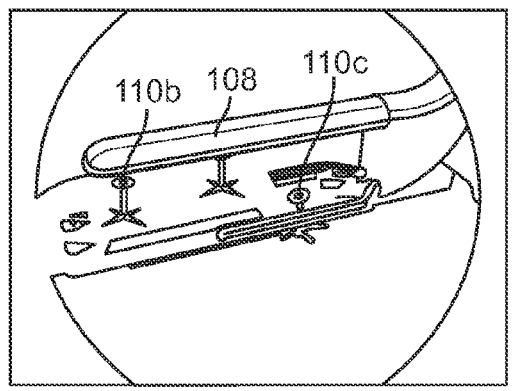
Figure 8:
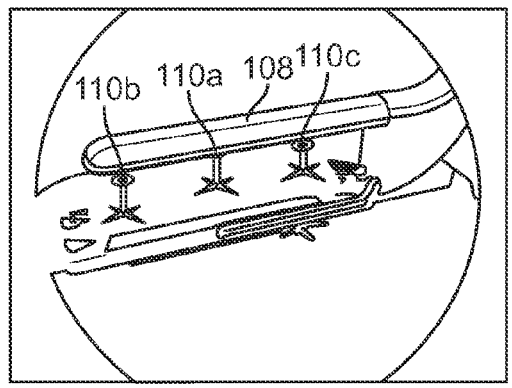

Then, as shown in FIG. 6, first the central tissue is brought up using anchor 110a. Any mechanical means can be used to raise the anchor 110a, such as a screw or clamp which can be operated by a doctor. The flexible bottom portion 104 of the anchoring mechanism 100 also rises with the anchors 110. Then, as shown in FIG. 7, the distal tissue is brought up using anchor 110b. Finally, proximal tissue 110c is brought up using anchor 110c. For purposes of the illustration, three anchors 110 are shown, although one or more can be used in the procedure. No specific order of raising the anchors 110 is required, and the anchors 110 can be raised in any order. In the preferred embodiment described above, the central anchor 110a is raised first, then the distal anchor 110b, and then the proximal anchor 110c.

Figure 9:
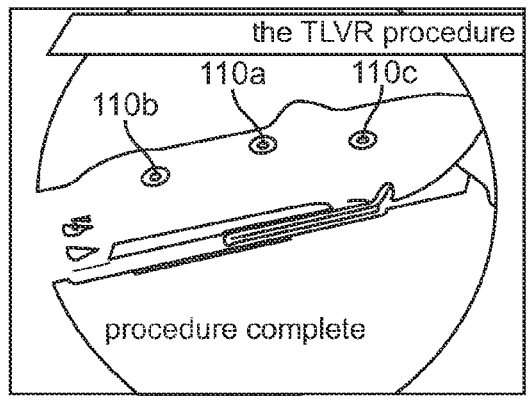

At the completion of the procedure, as shown in FIG. 9, the anchors 110 are secured. The anchors 110 can be secured using a screw thread means or any other means known in the art. The anchors 110 may be secured by a zip tag system, where the anchors are pulled together, or the anchors 110 can be clamped, or the anchors may even be glued with a biocompatible material. The anchors 110 may, of course, be secured by any other method known in the art and are not limited to the above. The top portion 108 is retracted, and the clips 105, 106 and bottom portion 104 are left in place with the anchors 110 on the dysfunctional cardiac tissue 103 to hold the tissue in place.

The dysfunctional cardiac tissue 103 is now excluded, and the volume of the ventricle is reduced to the appropriate volume with the aid of transesophageal echocardiography (TEE) by controlling the central, proximal and/or distal anchoring mechanism 100. The clips 105 can have a controlled drug release over an extended period of time.

Various other methods and devices are also possible for reducing ventricular volume in accordance with the present invention, which will be described below with respect to FIGS. 10-19.

Figure 10A:
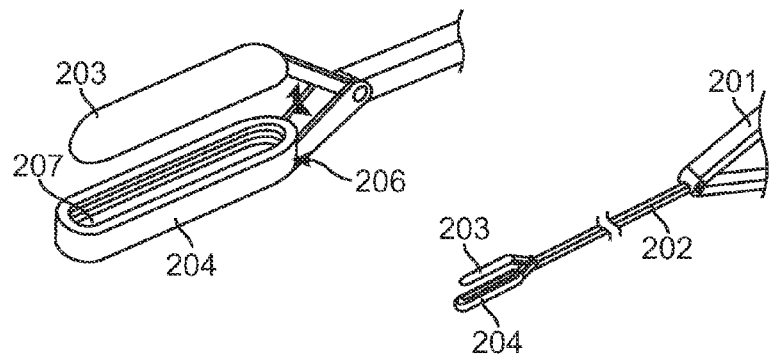
FIGS. 10-19 illustrate various other embodiments for reducing ventricular volume of a heart in accordance with the present invention.
Figure 10B:
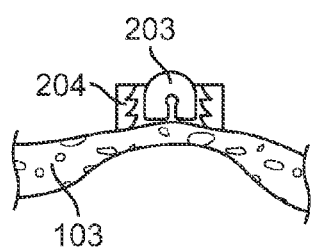
Figure 10C:
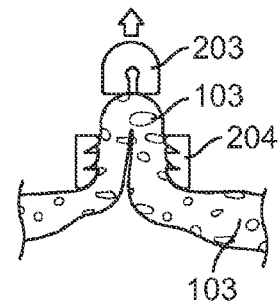

FIGS. 10(a)-10(c) illustrate a one way cartridge concept, where a long shaft 202 is connected to an actuator 201 at a distal end and a one-way cartridge at a proximal end. The one-way cartridge comprises a cartridge 204 and a suction head 203. The cartridge is connected to the long shaft 202 through a remotely detachable joint 206. In practice, the actuator and long shaft are inserted through a delivery tube to place the cartridge 203, 204 on dysfunctional cardiac tissue 103. The cartridge 204 is placed on the dysfunctional cardiac tissue 103, as seen in FIG. 10(b), and the suction head 204 lifts up the dysfunctional cardiac tissue 103 through the opening 207 of the cartridge 204. The cartridge 204 holds the dysfunctional cardiac tissue 103 in place and the suction cap 203 can be removed.

Figure 11:
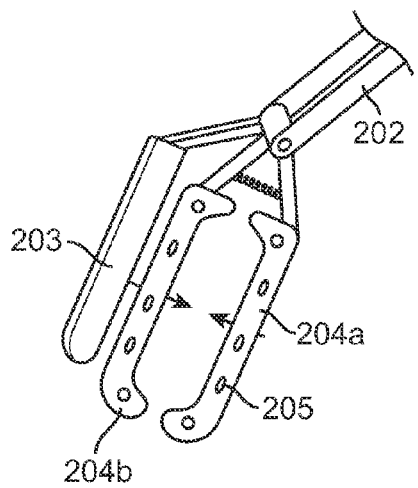

FIG. 11 shows a variation of the embodiment in FIG. 10, where the cartridge 204 has suction vents 205 along the top of the cartridge 204, and has interlocking parts 204a and 204b that make up the cartridge 204. Here, after the suction head 203 pulls up the dysfunctional cardiac tissue 103, the interlocking parts 204a and 204b can be pulled together to form a cartridge 204 to secure the dysfunctional cardiac tissue 103 in place.

Figure 12:
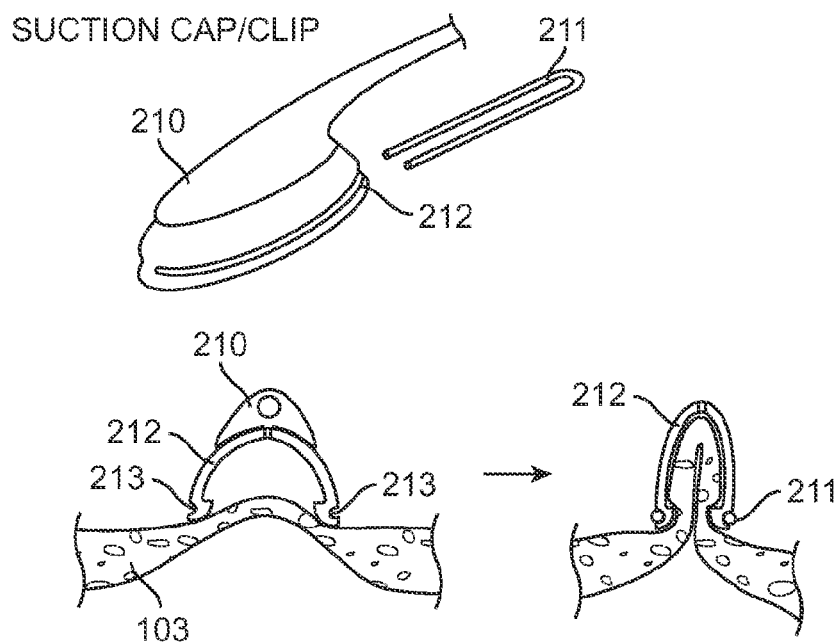

In FIG. 12, another variation of the embodiment above is described, which relies almost entirely on suction to exclude the dysfunctional cardiac tissue 103. Here, a suction cap/clip is shown having a suction cap 210, a molded silicon cap 212 and a locking clip 211. The suction cap/clip assembly is placed on the dysfunctional cardiac tissue 103 through a delivery tube, and the molded silicon cap 212 is placed on the dysfunctional cardiac tissue 103. The molded silicon cap is semi-circular in shape, and has slots 213 for the locking clip 211. The suction head 210 pulls up the dysfunctional cardiac tissue 103. The molded silicon cap 212 is then secured and squeezed in to hold the dysfunctional cardiac tissue 103 using locking clip 211 by placing the ends of the locking clip 211 through the slots 213. The suction cap 210 can then be removed, leaving the molded silicon cap 212 and locking clip 211 in place. Materials used for the cap 212 can be silicon or any other material known in the art, such as any bio-compatible material.

Figure 13:
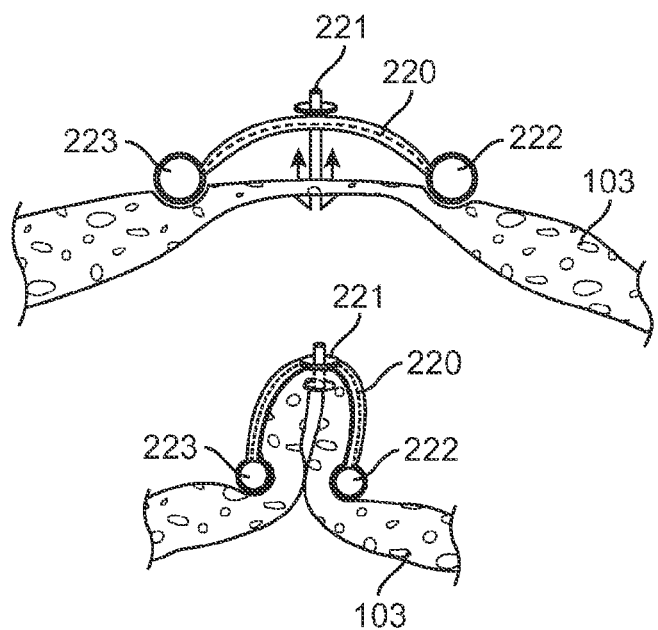

FIG. 13 shows another similar embodiment to FIG. 12, where a similar cap is placed on top of the dysfunctional cardiac tissue 103. An anchor 221 is driven through the cap 220 and through the dysfunctional cardiac tissue 103. The end of the anchor 221 has a deployment mechanism which expands once deployed through the wall of the dysfunctional cardiac tissue 103 to lock into place. The anchor 221 is then pulled up, and the cap 220 bends through forces exerted by the ends 222 and 223. The cap 220 can be such that it is under tension from ends 222 and 223, forcing it to compress and bend. Thus, once the anchor 221 is used to raise the dysfunctional cardiac tissue 103 up, the ends 222 and 223 hold the cap 220 in place, reducing the ventricular volume.

Figure 14:
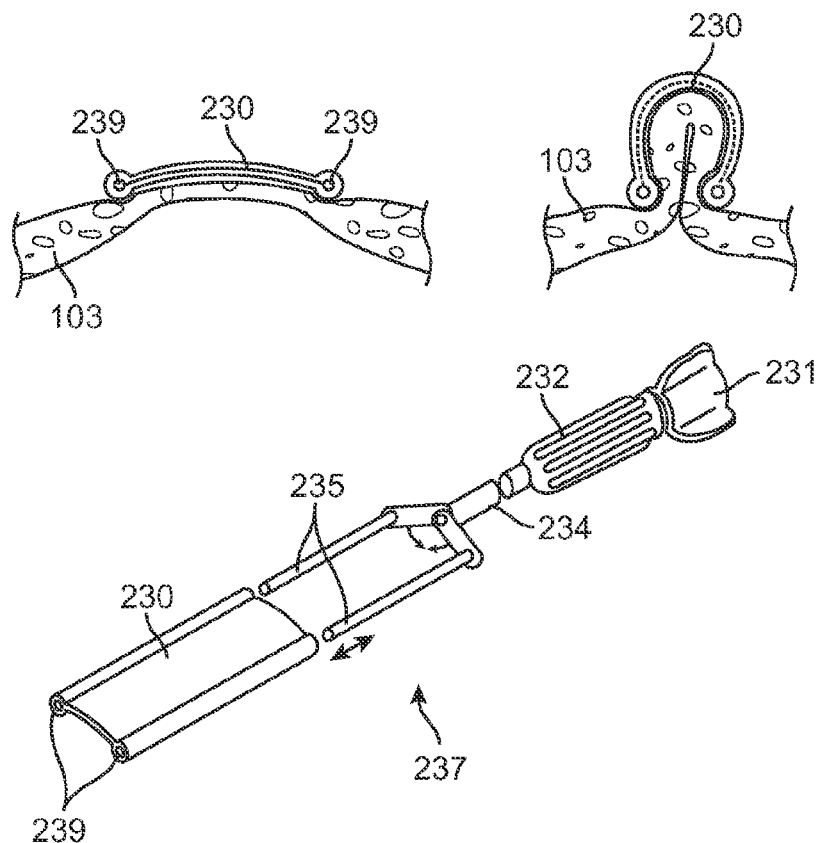

FIG. 14 shows a similar embodiment which is tightened using a tightening apparatus 237. First, a cap 230 is placed on top of dysfunctional cardiac tissue 103 using a tightening apparatus 237. The tightening apparatus comprises a knob 231, a grip 232, a long shaft 234, and force transmitting pins 235. The pins 235 connect to or go through the ends 239 of the cap 230. A spring is embedded inside the soft molded outer cover of the cap 230. First the knob 231 is turned to rotate the pins 235, which cause the ends 239 of the cap 230 to open up and open the cap 230 and place the spring cap 230 under tension, and the cap 230 is placed on top of the dysfunctional cardiac tissue 103. Then, the knob 231 is turned in the other direction to relax the spring and bring the cap 230 back to its normal position, thus squeezing in the dysfunctional cardiac tissue 103 between its ends 239. The spring in the cap 230 holds the dysfunctional cardiac tissue 103 in place and secures it into the cap 230.

Figure 15:
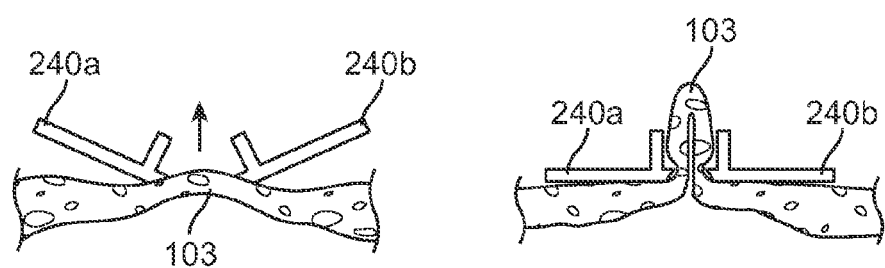

FIG. 15 shows another embodiment where two horizontal pieces 240a and 240b are placed on top of the dysfunctional cardiac tissue 103, and the dysfunctional cardiac tissue 103 is pulled up using a surgical instrument between the pieces 240a and 240b. Then, the two pieces 240a and 240b are pushed together to hold the dysfunctional cardiac tissue 103 in place, and secured by any type of locking means known in the art. The two pieces can be screwed together, nailed, tied, or any other means.

Figure 16:
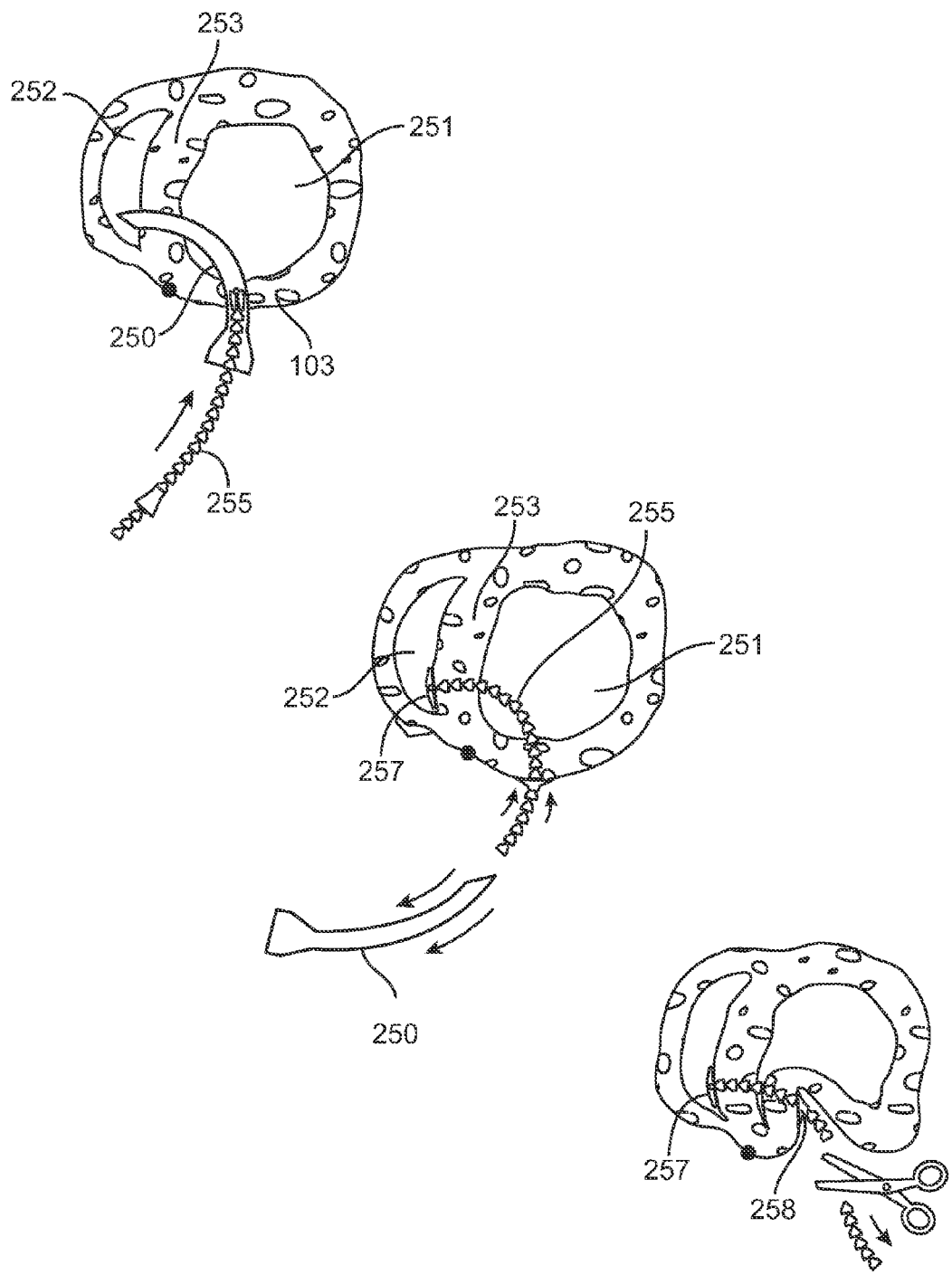
Figure 17:
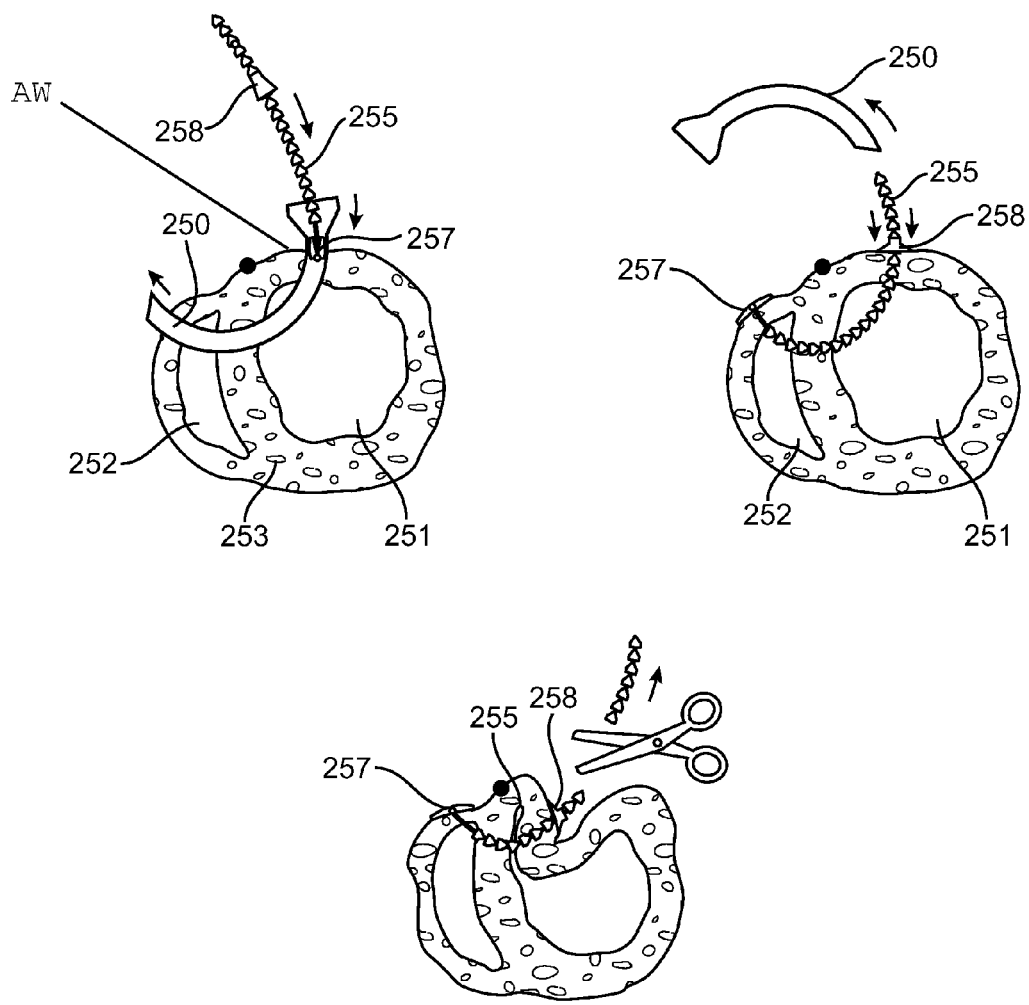
Figure 18:
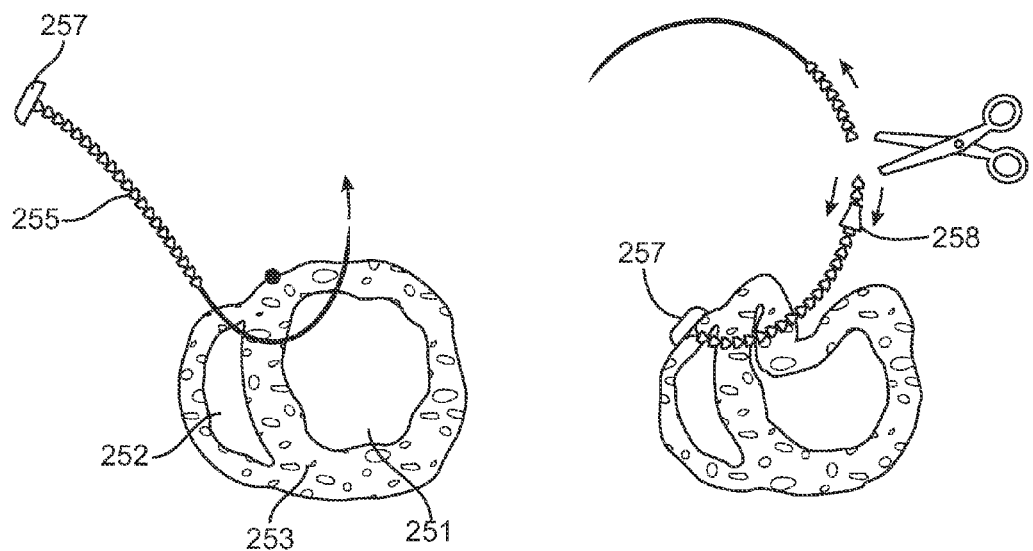

FIGS. 16-18 show a transventricular anchor system where an anchor is used through a hollow tube to reduce the ventricular volume of the heart.

In FIG. 16, a hollow tube 250 is used to pierce through dysfunctional cardiac tissue 103, going through the left ventricle 251, through the septum 253 and into the right ventricle 252. Then, an anchor 257 is deployed having a long ratcheting member 255 attached to it. One end of the anchor 257 is secured inside the right ventricle 252 against the wall of the septum 253. The hollow tube 250 is then removed. A locking member 258 is then secured against the ratcheting member 255 and pushed along the long ratcheting member until it locks into place along the locks placed alongside the ratcheting member 255. The locking member 258 can be pushed as far as required until the ventricular walls of the left ventricle 251 are folded enough to a surgeon's preference. Any excess length of the ratcheting member 255 can then be cut off and removed.

FIG. 17 shows a preferred variation of the transventricular approach from the left ventricle 251. Here, the hollow tube 250 is inserted through an posterior wall AW of the left ventricle 251, through the septum 253, and through the right ventricle 252. An anchor 257 is run through the hollow tube and secured to the outside of the right ventricle 252. The anchor 257 is connected to a long ratcheting member 255. The hollow tube is then removed, and a locking member 258 running along the length of the ratcheting member 255 is secured and pushed, locking it into place against the outer wall of the left ventricle, thus reducing the volume of the left ventricle, as can be seen in FIG. 17.

FIG. 18 shows another variation of the transventricular approach from the right ventricle 252. Again, a hollow tube 250 (not shown) is inserted through the right ventricle 252, through the septum 253 and through the left ventricle 251 all the way to the outer wall of the left ventricle 251. The hollow tube 250 is removed, leaving the ratcheting member 255 and anchor 257 behind, similar to the embodiments in FIGS. 16-17. The anchor 257 is secured against the outer wall of the right ventricle, and the locking member 258 is pushed along the length of the ratcheting member and against the wall of the left ventricle until tight, thus reducing the volume of the left ventricle, as can be seen in the figure.

Figure 19:
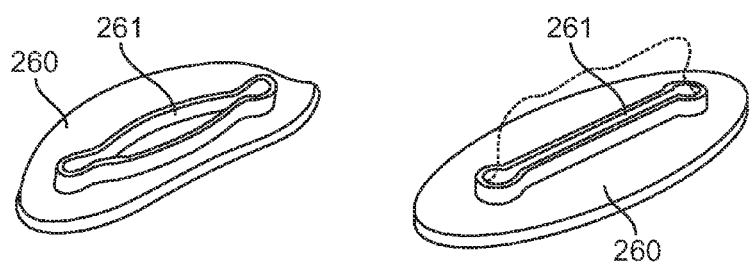

FIG. 19 shows a patch 260 with a deformable slit 261. This device is made from two components: the deformable slit 261 is formed from fully annealed stainless steel or other malleable metallic alloy and the attached patch is a woven fabric material, such as Dacron. The initial shape of the slit 261 has a shape similar to an elongated ellipse. The patch 260 with the deformable slit 261 is placed on the heart with the center of the slit preferably 2-3 cm from the LAD and the long axis of the slit generally parallel to the LAD. The dysfunctional tissue 103 is pulled through the slit using either one or more anchors placed through the tissue 103, or using the previously described suction device. After the desired amount of tissue 103 has been pulled through the opening, a surgical tool is used to approximate the long edges of the deformable slit 261 to hold the gathered tissue 103 in place. The effective removal of tissue from the ventricular volume and the gathering of the tissue edges together reduces the volume and short-axis diameter of the left ventricle as can be seen from the figure. The gathered tissue 103 is further secured in place by sewing the cloth material to the epicardial surface of the tissue 103 and by suturing the tissue 103 to the malleable slit 261.

The present invention provides several advantages that solve the problems with prior art methods. The method may be performed minimally invasively, which is less traumatic to the patient than an open-chest and open-heart surgical technique when reducing the volume of the ventricles (and thus reducing the tension in the heart wall and reversing the disease process of a failing heart).

Further, the clips/clamps employ small quantities of drug to be administered over an extended period of time to the heart tissue, thus avoiding the pitfalls associated with systemic delivery of a drug. The present invention avoids problems associated with bolus injection of a drug, such as delivery of an amount of drug to the cardiac tissue, which is too high and which therefore may have deleterious effects on the cardiac tissue. Another advantage is that it provides long-term delivery of a drug to the pericardium or myocardial tissue, with even delivery rate. Extended delivery of the drugs to the cardiac tissue can be achieved during the placement of the clips or clamps, without the need for invasive surgery, thereby reducing trauma to the patient.

One principal advantage of the system and method of the present invention is the ability to directly monitor left ventricular function without opening the left side of the heart. The system and method of the present invention is advantageously employed to measure cardiac dimensions in real time and to either record or transmit these values for monitoring purposes or to use these values as feedback to modify the delivery of electrical or pharmacological therapy, particularly in the treatment of heart failure. Further, the system and method of the present invention can be advantageously employed in the detection of electromechanical association during pacing or arrhythmias, differentiation of hemodynamically significant and insignificant ventricular tachycardias, monitoring of cardiac output, ventricular volume, determining the need for aggressive and less aggressive pharmacological therapies, and the like.

The above descriptions of the present invention are specific embodiments of the present invention and are not limited to the above descriptions and uses. Various sizes, numbers and types of anchors can be used. Various clips and/or clamps can be used in the anchoring mechanism. Any type of drugs can be released by the clips/clamps over various times. The anchoring system elements are not limited to what is described above, and any type of other anchoring elements can be used to deploy anchors into the dysfunctional tissue 103.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for reducing a volume of a heart, the method comprising:
   from a posterior approach, inserting a curved hollow tube through a posterior left ventricle wall into a left ventricle and through a septum into a right ventricle so that a curved lumen of the hollow tube extends from outside the heart and posterior of the heart, through the left ventricle wall, and then curves through the septum and opens into the right ventricle;
   deploying an anchor connected to a ratchet mechanism through the hollow tube by advancing the anchor within the curved lumen from outside the heart, through the left ventricle wall and the septum, and into the right ventricle;
   removing the hollow tube so that the ratchet mechanism extends from the deployed anchor, through the ventricle wall and the septum, and outside the patient;
   securing the anchor against the septum inside the right ventricle by securing a locking mechanism to the ratchet mechanism, and by advancing the locking mechanism along the ratchet mechanism toward the anchor; and
   locking the locking mechanism against the left ventricle wall so that a volume of the left ventricle of the heart is reduced.

2. The method of claim 1, wherein when the curved hollow tube is inserted through the posterior left ventricle wall into the left ventricle and through the septum into the right ventricle, the curved hollow tube has substantially the same radius of curvature from the portion of the curved hollow tube traversing the left ventricle wall to the portion of the curved hollow tube traversing the septum.

3. A method for reducing a volume of a heart, the method comprising:
   cutting a subxiphoid incision to create an opening to access the ventricles of the heart;
   inserting a curved hollow tube through a left ventricle wall into the left ventricle, through a septum, through the right ventricle, and through a right ventricle wall so that a curved lumen of the hollow tube extends from outside the heart through the left ventricle wall, then curves through the septum and right ventricle wall, and opens back outside of the heart;
   deploying an anchor connected to a ratchet mechanism through the hollow tube by advancing the anchor within the curved lumen from outside the heart, through the left ventricle wall, the septum, and the right ventricle wall to the outside of the heart;
   securing the anchor against an outer surface of the right ventricle wall by securing a locking mechanism to the ratchet mechanism, and by advancing the locking mechanism along the ratchet mechanism toward the anchor; and
   locking the locking mechanism against the outer left ventricle wall so that a volume of the left ventricle of the heart is reduced.

4. The method of claim 3, wherein when the curved hollow tube is inserted through the left ventricle wall into the left ventricle, through the septum, through the right ventricle, and through the right ventricle wall, the curved hollow tube has substantially the same radius of curvature from the portion of the curved hollow tube traversing the left ventricle wall to the portion of the curved hollow tube traversing the septum and to the portion of the curved hollow tube traversing the right ventricle wall.

5. A method for reducing a volume of a heart, the method comprising:
   from a posterior approach, inserting a curved hollow tube through a posterior left ventricle wall into a left ventricle and through a septum into a right ventricle so that a curved path of the hollow tube extends from outside the heart and posterior of the heart, through the left ventricle wall, and then curves through the septum and opens into the right ventricle;
   deploying an anchor connected to a ratchet mechanism using the hollow tube by advancing the anchor along the curved path from outside the heart, through the left ventricle wall and the septum, and into the right ventricle;
   removing the hollow tube;
   securing the anchor against the septum inside the right ventricle by securing a locking mechanism to the ratchet mechanism, and by advancing the locking mechanism along the ratchet mechanism toward the anchor; and
   locking the locking mechanism against the left ventricle wall so that a volume of the left ventricle of the heart is reduced.

6. The method of claim 5, wherein when the curved hollow tube is inserted through the posterior left ventricle wall into the left ventricle and through the septum into the right ventricle, the curved hollow tube has substantially the same radius of curvature from the portion of the curved hollow tube traversing the left ventricle wall to the portion of the curved hollow tube traversing the septum.

7. A method for reducing a volume of a heart, the method comprising:
   cutting a subxiphoid incision to create an opening to access the ventricles of the heart;
   inserting a curved hollow tube through a left ventricle wall into the left ventricle, through a septum, through the right ventricle, and through a right ventricle wall so that a curved path of the hollow tube extends from outside the heart through the left ventricle wall, then curves through the septum and right ventricle wall, and opens back outside of the heart;
   deploying an anchor connected to a ratchet mechanism using the hollow tube by advancing the anchor along the curved path from outside the heart, through the left ventricle wall, the septum, and the right ventricle wall to the outside of the heart;
   securing the anchor against an outer surface of the right ventricle wall by securing a locking mechanism to the ratchet mechanism, and by advancing the locking mechanism along the ratchet mechanism toward the anchor; and
   locking the locking mechanism against the outer left ventricle wall so that a volume of the left ventricle of the heart is reduced.

8. The method of claim 7, wherein when the curved hollow tube is inserted through the left ventricle wall into the left ventricle, through the septum, through the right ventricle and through the right ventricle wall, the curved hollow tube has substantially the same radius of curvature from the portion of the curved hollow tube traversing the left ventricle wall to the portion of the curved hollow tube traversing the septum and to the portion of the curved hollow tube traversing the right ventricle wall.

* * * * *